United States Patent [19]

Kump

[11] 4,379,149
[45] Apr. 5, 1983

[54] PROCESS FOR INTRODUCING AN OXYGEN-CONTAINING FUNCTIONAL GROUP INTO ANSAMYCINS

[75] Inventor: Wilhelm Kump, Biel-Benken, Switzerland

[73] Assignee: Ciba-Geigy Corporation, Ardsley, N.Y.

[21] Appl. No.: 304,457

[22] Filed: Sep. 22, 1981

Related U.S. Application Data

[63] Continuation of Ser. No. 167,970, Jul. 14, 1980, abandoned.

[51] Int. Cl.³ .................. A61K 31/395; C07D 491/08
[52] U.S. Cl. .............................. 424/244; 260/239.3 P
[58] Field of Search .................. 260/239.3 P; 424/244

[56] References Cited

U.S. PATENT DOCUMENTS 3,923,791  12/1975  Celmer ........................ 260/239.3 P

OTHER PUBLICATIONS

Morrison and Boyd, "Organic Chemistry", 3rd Ed., (Allyn and Bacon), (1973), pp. 456-458.

*Primary Examiner*—Robert T. Bond
*Attorney, Agent, or Firm*—Michael W. Glynn

[57] ABSTRACT

3-Hydroxyrifamycin S and its new analogues with an etherified or esterified 3-hydroxyl group of the formula

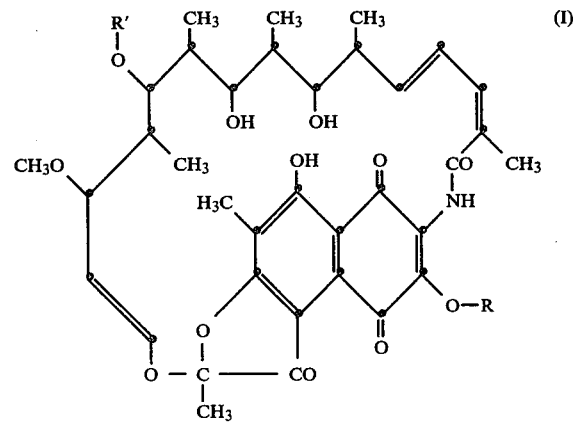

in which each of R and R' represents a hydrogen atom, or R' represents acetyl and R represents hydrogen, an optionally substituted hydrocarbyl or the acyl radical of a carboxylic acid, and also the corresponding compounds of the SV series, are obtained by a novel process in which 3-bromorifamycin S is treated with a reagent ROH, in which R has the meanings mentioned above, or with a salt thereof, in a neutral to weakly basic medium. The final products are primarily suitable as antibiotics for combating microbial infections and/or as intermediates for the manufacture of the same.

13 Claims, No Drawings

PROCESS FOR INTRODUCING AN OXYGEN-CONTAINING FUNCTIONAL GROUP INTO ANSAMYCINS

This is a continuation of application Ser. No. 167,970 filed on July 14, 1980, now abandoned.

The invention relates especially to the introduction of an oxygen-containing functional group into the molecule of ansamycins, namely a free, etherified or esterified hydroxyl group into the 3-position of ansamycins of the rifamycin type.

As recently discovered, cf. our European Patent Application No. 80810016.8, the new 3-hydroxyrifamycin S obtained by fermentation has favourable antibiotic, especially antimicrobial, properties, which are similar to those of rifamycin S in character.

In the search for an alternative, purely chemical access to this compound, the present process according to the invention was discovered, which, in a surprisingly simple manner, is not only able to yield the desired already known 3-hydroxyrifamycin S, but also provides access to a broad group of new rifamycin analogues which are distinguished by a structural feature not previously known, namely a free, etherified or esterified hydroxyl group in the 3-position.

The final products obtainable according to the invention are especially compounds of the formula

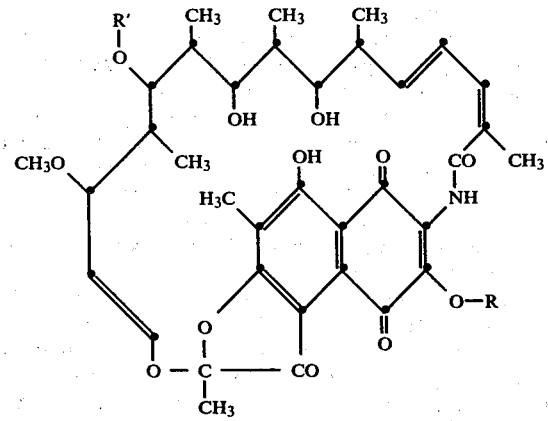

in which each of R and R' represents a hydrogen atom, or R' represents acetyl and R represents hydrogen, an optionally substituted hydrocarbyl or the acyl radical of a carboxylic acid, and the corresponding rifamycin SV derivatives having the 1,4-hydroquinone structure.

As a result of the very close relationship between the 1,4-quinone and 1,4-hydroquinone from corresponding to rifamycin S and SV) and the ease with which the two can be interconverted, both forms are included throughout unless specifically stated otherwise.

The hydrocarbyl radical (hydrocarbon radical) is an acyclic, carbocyclic or carbocyclic-acyclic hydrocarbon radical, which has preferably at most 18 carbon atoms and may be saturated or unsaturated, unsubstituted or substituted. In place of one, two or more carbon atoms, it may also carry hetero atoms, such as especially oxygen, sulphur and nitrogen, and also phosphorus and silicon, and thus represent a heterocyclic radical (heterocyclyl radical) or a heterocyclic-acyclic radical.

The term "unsaturated radicals" applies to those radicals that contain one or more multiple bonds, such as double and triple bonds. Cyclic radicals in which at least one 6-membered carbocyclic ring or 5- to 8-membered heterocyclic ring contains the maximum number of non-cumulative double bonds are called aromatic. Carbocyclic radicals in which at least one ring is present as a 6-membered aromatic ring (i.e. benzene ring) are called aryl radicals.

Unless otherwise specified, in the present disclosure organic radicals denoted by "lower" contain at most 7, preferably at most 4, carbon atoms.

An acyclic hydrocarbon radical is especially a straight or branched lower alkyl, lower alkenyl, lower alkadienyl or lower alkynyl radical. Lower alkyl is, for example, methyl, ethyl, n-propyl, isopropyl, n-butyl, isobutyl, sec.-butyl or tert.-butyl, and also n-pentyl, isopentyl, n-hexyl, isohexyl or n-heptyl; lower alkenyl is, for example, vinyl, allyl, propenyl, isopropenyl, 2- or 3-methallyl and but-2-enyl or but-3-enyl; lower alkynyl is, for example, propargyl or but-2-ynyl.

A carbocyclic hydrocarbon radical is especially a monocyclic, bicyclic or polycyclic cycloalkyl, cycloalkenyl or cycloalkadienyl radical, or a corresponding aryl radical containing aromatic rings. Radicals having at most 12 ring carbon atoms and from 3- to 8-, preferably 5- and/or 6-membered rings are preferred, wherein they may also carry one or more acyclic radicals, for example those mentioned above, and especially the lower alkyl radicals, or other carbocyclic radicals. Carbocyclic-acyclic radicals are those in which an acyclic radical, especially one having at most 7, preferably at most 4, carbon atoms, carries one or more carbocyclic, optionally aromatic radicals of the above definition. Special mention should be given to cycloalkyl-lower alkyl and aryl-lower alkyl radicals and their analogues that are unsaturated in the ring and/or side chain.

Cycloalkyl is, for example, cyclopropyl, cyclobutyl, cyclopentyl, cyclohexyl, cycloheptyl and cyclooctyl, also bicyclo[2,2,2]octyl, 2-bicyclo[2,2,2]heptyl and adamantyl, furthermore also 1-, 2- or 3-methylcyclopentyl, 4-tert.-butylcyclohexyl, 4,4-dimethylcyclohexyl, 2,4,6-trimethylcyclohexyl, and 2,4,4,6-tetramethylcyclohexyl; cycloalkenyl is, for example, one of the cycloalkyl radicals already mentioned which carries a double bond in the 1-, 2- or 3-position, such as 1-, 2- or 3-cyclopentenyl and 1-, 2- or 3-cyclohexenyl. Cycloalkyl-lower alkyl or cycloalkyl-lower alkenyl is, for example, cyclopropyl-, cyclopentyl-, cyclohexyl- or cycloheptyl-methyl, -1- or -2-ethyl or -vinyl, -1-, -2- or -3-propyl or -allyl, also dicyclohexylmethyl and tricyclohexyl-methyl; cycloalkenyl-lower alkyl or cycloalkenyl-lower alkenyl is, for example, 1- 2- or 3-cyclopentenyl- or 1-, 2- or 3-cyclohexenyl-methyl, -1- or -2-ethyl or -vinyl, -1-, -2-or -3-propyl or -allyl.

An aryl radical is especially a phenyl, also a naphthyl, such as 1- or 2-naphthyl, a biphenylyl, such as especially 4-biphenylyl, also an anthryl, fluorenyl and azulenyl. Preferred aryl-lower alkyl and aryl-lower alkenyl radicals are, for example, phenyl-lower alkyl or phenyl-lower alkenyl, for example benzyl, 1- or 2-phenylethyl, 1-, 2- or 3-phenylpropyl, diphenylmethyl (i.e. benzhydryl), trityl and 1- or 2-naphthylmethyl, and styryl or cinnamyl.

Heterocyclic radicals, including the heterocyclic-acyclic radicals, are especially monocyclic, and also bicyclic or polycyclic, aza-, thia-, oxa-, thiaza-, thiadiaza-, oxaza-, diaza-, triaza- or tetraza-cyclic radicals of an aromatic character, furthermore, corresponding partially or wholly saturated heterocyclic radicals of this kind, wherein such radicals may optionally carry, for example like the above-mentioned carbocyclic or aryl radicals, other acyclic, carbocyclic or heterocyclic radicals, and may be mono-, di- or poly-substituted. The acyclic part in heterocyclic-acyclic radicals has, for example, the meaning specified for the corresponding carbocyclic-acyclic radicals. These are, in particular, unsubstituted or substituted monocyclic, monoaza-, monothia- or mono-oxacylic radicals, such as aziridinyl, oxiranyl and thiiranyl, and especially heterocyclic radicals of an aromatic character, such as pyrryl, for example 2-pyrryl or 3-pyrryl, pyridyl, for example 2-, 3- or 4-pyridyl, also thienyl, for example 2- or 3-thienyl, or furyl, for example 2-furyl; bicyclic monoaza-, monooxa- or monothia-cyclic radicals, such as indolyl, for example 2- or 3-indolyl, quinolinyl, for example 2-or 4-quinolinyl, isoquinolinyl, for example 1-isoquinolinyl, benzofuranyl, for example 2- or 3-benzofuranyl, or benzothienyl, for example 2- or 3-benzothienyl; monocyclic diaza-, triaza-, tetraza-, oxaza-, thiaza- or thiadiaza-cyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazoly, oxazolyl, for example 2-oxazolyl, isoxazolyl, for example 3- or 4-isoxazolyl, thiazolyl, for example 2-thiazolyl, isothiazolyl, for example 3- or 4-isothiazolyl or 1,2,4- or 1,3,4-thiadiazolyl, for example 1,2,4-thiadiazol-3-yl or 1,3,4-thiadiazol-2-yl; or bicyclic diaza-, oxaza- or thiaza-cyclic radicals, such as benzimidazolyl, for example 2-benzimidazolyl, benzoxazolyl, for example 2-benzoxazolyl, or benzthiazolyl, for example 2-benzthiazolyl. Corresponding partially or wholly saturated radicals are, for example, tetrahydrothienyl, such as 2-tetrahydrothienyl, tetrahydrofuryl, such as 2-tetrahydrofuryl, pyrrolidyl, such as 2-pyrrolidyl, tetrahydropyridyl, such as $\Delta^1$-, $\Delta^2$- or $\Delta^3$-piperideinyl, or piperidyl, such as 2-, 3- or 4-piperidyl, furthermore also morpholinyl, thiomorpholinyl, piperazinyl and N,N'-bis-lower alkyl piperazinyl, such as especially N,N'-dimethylpiperazinyl. These radicals may also carry one or more acyclic, carbocyclic or heterocyclic radicals, especially those mentioned above. Heterocyclic-acyclic radicals are derived especially from acyclic radicals having at most 7, preferably at most 4, carbon atoms, for example from those mentioned above, and may carry one, two or more heterocyclic radicals, for example those mentioned above.

As already mentioned, a hydrocarbyl (including a heterocyclyl) can be substituted by one, two or more identical or different substitutents; the following substituents in particular may be considered: free, etherified and esterified hydroxyl groups; mercapto and lower alkylthio and optionally substituted phenylthio groups; halogen atoms, such as chlorine and fluorine, and also bromine and iodine; formyl (i.e. aldehydo) and keto groups, also as acetals and ketals; azido and nitro groups; primary, secondary and, preferably, tertiary amino groups, primary or secondary amino groups protected by conventional protecting groups, such as suitable acylamino groups and diacylamino groups; also free sulphamino groups and sulphamino groups present in salt form, such as alkali metl salt form, free and functionally modified carboxyl groups, such as carboxyl groups present in salt form or esterified carboxyl groups; carbamoyl, ureidocarbonyl or guanidinocarbonyl groups optionally carrying one or two hydrocarbon radicals, and cyano groups; also optionally functionally modified sulpho groups, such as sulphamoyl groups or sulpho groups present in salt form.

An etherified hydroxyl group present as substituent in the hydrocarbyl is, for example, a lower alkoxy group, such as the methoxy, ethoxy, propoxy, isopropoxy, butoxy and tert.-butoxy group, which may also be substituted. Thus, such a lower alkoxy group may be substituted by halogen atoms, especially in the 2-position, such as in the 2,2,2-trichloroethoxy, 2-chloroethoxy or 2-iodoethoxy radical, or by lower alkoxy radicals, especially in the 1-position, such as in the 1-butoxyethoxy radical, or in the 2-position, such as in the 2-methoxyethoxy radical. Furthermore, such etherified hydroxyl groups are also optionally substituted phenoxy radicals and phenyl-lower alkoxy radicals, such as especially benzyloxy, benzhydryloxy and triphenylmethoxy (trityloxy) radicals, and also heterocyclyloxy radicals, such as especially 2-tetrahydrofuranyloxy and 2-tetrahydropyranyloxy radicals. Etherified hydroxyl groups are in this connection also silylated hydroxyl groups, as are present, for example, in tri-lower alkylsilyloxy groups, such as trimethylsilyloxy or dimethyl-tert.-butylsilyloxy or phenyl-di-lower alkylsilyloxy or lower alkyldiphenylsilyloxy groups.

An esterified hydroxyl groups present as substituent in hydrocarbyl is a group in which the hydrogen atom of the hydroxyl group is replaced by the acyl radical —$COR^1$ defined further below, or is a lactonised hydroxyl group.

An esterified carboxyl group present as substituent in hydrocarbyl is a group in which the hydrogen atom is replaced by one of the above-characterised hydrocarbon radicals, preferably a lower alkyl or phenyl-lower alkyl radical; examples of an esterified carboxyl group are especially the methoxycarbonyl, ethoxycarbonyl, tert.-butoxycarbonyl or benzoyloxycarbonyl groups, and also a lactonised carboxyl group.

A primary amino group —$NH_2$ as substituent of hydrocarbyl is preferably present in protected form as an acylamino group, corresponding to this group, of the formula —NH—Ac, in which Ac has the meaning characterised below. A secondary amino group carries a, preferably unsubstituted, hydrocarbon radical of the above type instead of one of the two hydrogen atoms, and is preferably present in a protected form as an acylamino group derived therefrom, which additionally carries a monovalent acyl radical Ac characterised below.

The acyl radical Ac serving as amino-protecting group is preferably derived from a carbonic acid semi-derivative and is preferably an optionally substituted, (especially by lower alkyl, lower alkoxy, nitro and/or halogen) lower alkoxycarbonyl or aryl-lower alkoxycarbonyl, such as methoxycarbonyl, ethoxycarbonyl, tert.-butoxycarbonyl, 2,2,2-trichloroethoxycarbonyl, 2-iodethoxycarbonyl, benzyloxycarbonyl, 2-phenyl-2-propoxycarbonyl, 2-p-tolyl-2-propoxycarbonyl, 2-p-biphenylyl-2-propoxycarbonyl, 1,1-diphenylethoxycarbonyl or p,p'-dimethoxybenzhydryloxycarbonyl. Especially to be emphasized is also a 2-(trihydrocarbylsilyl)ethoxycarbonyl, such as 2-triphenylsilylethoxycarbonyl, 2-(dibutyl-methyl-silyl)ethoxycarbonyl, and especially 2-trimethylsilylethoxycarbonyl, which can be split off especially readily and selectively with fluorides of quaternary bases.

A tertiary amino group occurring as substituent in hydrocarbyl is characterised by the formula

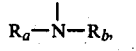

wherein $R_a$ and $R_b$ represent monovalent hydrocarbon radicals (including the analogous heterocyclic radicals) which may be identical or different and correspond to the above-characterised unsubstituted hydrocarbyl radical. The two hydrocarbon radicals $R_a$ and $R_b$ may be joined together by a carbon-carbon bond or by an oxygen, sulphur or optionally substituted nitrogen atom, and together with the nitrogen atom of the amino group form a nitrogen-containing heterocyclic ring. Examples of especially preferred free amino groups are the following: di-lower alkylamino, such as dimethylamino, diethylamino, pyrrolidino, piperidino, morpholino, thiomorpholino and piperazino or 4-methylpiperazino, diphenylamino and dibenzylamino optionally substituted by lower alkyl, lower alkoxy, halogen and/or nitro: examples of the protected amino groups are then especially halo-lower alkoxycarbonylamino, such as 2,2,2-trichloroethoxycarbonylamino, phenyl-lower alkoxycarbonylamino, such as 4-methoxybenzyloxycarbonylamino, and also 2-(trihydrocarbylsilyl)ethoxycarbonylamino, such as 2-triphenylsilylethoxycarbonylamino, 2-(dibutyl-methyl-silyl)ethoxycarbonylamino and 2-trimethylsilylethoxycarbonylamino.

The acyl radical of a carboxylic acid is characterised by the partial formula $R^1CO-$. In this formula, $R^1$ may either represent hydrogen and thus form the formyl radical, or may have one of the above-mentioned general and preferred meanings of the hydrocarbyl radical and thus is derived from an optionally substituted acyclic, carbocyclic, carbocyclic-acyclic, heterocyclic or heterocyclic-acyclic carboxylic acid. Especially preferred are acyl radicals of the following monocarboxylic acids having at most 18 carbon atoms: acyclic carboxylic acids, especially lower alkanecarboxylic acids, such as propionic, butyric, isobutyric, valeric, isovaleric, caproic, trimethylacetic, oenanthic and diethylacetic acids, and especially acetic acid, but also corresponding halogenated lower alkanecarboxylic acids, such as chloroacetic acid, bromoacetic or α-bromoisovaleric acid; carbocyclic or carbocyclic-acyclic monocarboxylic acids, for example cyclopropane-, cyclobutane-, cyclopentane- and cyclohexane-carboxylic acid, or the cyclopropane-, cyclobutane-, cyclopentane- or cyclohexane-acetic or propionic acids; aromatic carboxylic carboxylic acids, for example benzoic acid, which may be substituted one or more times by halogens, such as fluorine, chlorine, bromine and/or hydroxy, lower alkoxy, lower alkyl and nitro: aryl or aryloxy-lower alkanecarboxylic acids and their analogues that are unsaturated in the chain, for example optionally substituted, (for example as specified above for benzoic acid) phenylacetic or phenoxyacetic acids, phenylpropionic acids and cinammic acids; and heterocyclic acids, for example furan-2-carboxylic acid, 5-tert.-butylfuran-2-carboxylic acid, 5-bromofuran-2-carboxylic acid, thiophene-2-carboxylic acid, nicotinic or isonicotinic acid, 4-pyridinepropionic acid, and pyrrol-2- or -3-carboxylic acids optionally substituted by lower alkyl radicals; furthermore also corresponding α-amino acids, especially the naturally occurring amino acids of the L-series, for example glycine, phenylglycine, proline, leucine, valine, tyrosine, histidine and asparagine, preferably in an N-protected form, that is to say, in a form in which the amino group is substituted by a conventional amino-protecting group, for example one of those mentioned above. Carboxylic acids, which may also be considered are in particular those in which $R^1$ represents a hydrocarbyl which is substituted by an optionally functionally modified carboxyl, that is, one which is derived from a dicarboxylic acid having at most 12 carbon atoms and which is based on one of the above-characterised optionally substituted acyclic, carbocyclic, carbocyclic-acyclic, heterocyclic and heterocyclic-acyclic radicals. The following dicarboxylic acids may be mentioned by way of example: oxalic acid, malonic acid, mono- or di-lower alkylmalonic acids, succinic acid, glutaric acid, adipic acid, maleic acid, itaconic acid, citraconic acid, angelic acid, 1,1-cyclopentane- or 1,1-cyclohexane-dicarboxylic acid, a phthalic, quinolinic or phenylsuccinic acid optionally substituted by halogen, such as fluorine, chlorine or bromine, and/or by lower alkyl, lower alkoxy and nitro, and also tartronic acid, mesoxalic acid, oxalacetic acid, malic acid, tartaric acid, a tartaric acid esterified or etherified at the hydroxyl groups, glutamic acid and aspartic acid, wherein the two last-mentioned acids are present preferably with protected amino groups. As already stated, the second carboxyl group may be not only free but also functionally modified, for example as an ester with an alcohol, or as a salt, preferably as a physiologically tolerable salt, with a salt-forming basic component. Especially suitable are metal salts or ammonium salts, such as alkali metal and alkaline earth metal salts, for example sodium, potassium, magnesium or calcium salts, and ammonium salts with ammonia or suitable organic amines. These include especially tertiary monoamines and heterocyclic bases, for example triethylamine, tri-(2-hydroxyethyl)amine, 1-ethylpiperidine, and also pyridine, collidine or quinoline.

The process according to the invention is characterised in that in 3-bromorifamycin S of the formula

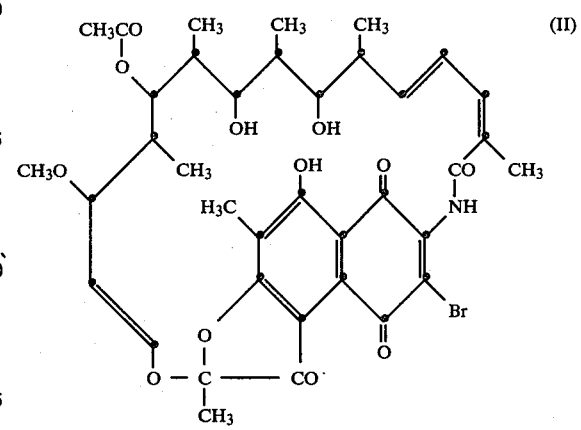

(II)

bromine is exchanged for the above-defined group OR and the product is isolated in the form of a derivative of the S series or SV series. The exchange is preferably carried out by treating the compound of the formula II with a compound of the formula ROH (III), in which R has the meanings given above, or with a salt thereof, in a neutral to basic medium and optionally in the presence of a hydrogen bromide-binding agent, and/or an organic solvent.

The practical implementation of the process according to the invention is effected under the conventional general conditions of preparative organic chemistry: normally, the operation is carried out at atmospheric pressure or at a slightly elevated pressure, for example in the case of readily volatile solvents to achieve higher reaction temperatures; these lie between room temperature and the boiling temperature of the mixture, especially between approximately 20° and approximately 140° C., preferably between approximately 90° and approximately 120° C. Usually, an excess, for example approximately 2 to 15 mole equivalents, of exchange agent of the formula III is sued, and optionally also of auxiliaries, and the reaction is carried out in homogeneous or heterogeneous phase, that is to say, in solution or suspension, in the latter case preferably whilst stirring. Normally, the reaction time extends from approximately 30 minutes to approximately one day, which is dependent on the reaction temperature and the other conditions, and also on the specific properties of the component III. The progress of the reaction can be followed by the conventional analytical methods, especially by spectroscopy and thin-layer chromatography.

The symbol R in the exchange reagent of the formula ROH (III) may have each of the above-mentioned general and preferred meanings. The starting material of the formula II, i.e. 3-bromorifamycin S, is known.

As auxiliary agent to bind hydrogen bromide there may be used in principle any basic compounds such as, on the one hand, organic nitrogen-containing bases, for example tertiary amines of the triethylamine, ethyl diisopropylamine, N-ethylpiperidine or N,N'-dimethylpiperazine type, or aromatic heterocyclic bases of the pyridine, collidine or quinoline type, and, on the other hand, inorganic compounds having a basic reaction, especially alkali metal salts of weak or medium-strength acids, for example those mentioned further below, and also analogous salts of carboxylic acids; furthermore also ion exchangers, such as, especially, cation exchangers in the alkali metal cycle, such as the Na— or K— cycle, or anion exchangers in the OH cycle. Finally, neutral reacting nitrogen-containing compounds may serve, at least in part, for this purpose, which at the same time are frequently also advantageous solvents, for example carboxylic acid amides, especially lower aliphatic carboxylic acid amides, such as formamide, N,N'-dimethylformamide, acetamide and N,N-dimethylacetamide, and cyclic amides, such as N-methylpyrrolidone, and also amido derivatives of carbonic acid, such as urethanes. In choosing the specific agent, it is necessary always to take into account the great sensitivity of the rifamycin structure and to avoid those agents which would lead to side reactions. The above-mentioned basic compounds can serve to comply with the basic reaction of the medium; the conventional buffers may be used specifically for this purpose.

It should also be noted that one and the same reaction component can also take on the function of other or several components or auxiliaries, for example the reactant of the formula III may be used simultaneously as solvent, or a basic component may serve not only to initiate the basic reaction but may also at the same time bind hydrogen bromide by the buffer effect, or even, like, for example a metal salt of a carboxylic acid, in addition to these two functions may also be the actual exchange agent III.

Although the exchange reaction is always based on the same principle and the reaction is performed according to a uniform basic scheme, for an optimal result it is necessary to take into account the character of the reaction components when carrying out practical operation, in particular the character of the reactant of the formula III. According to the preceding definition of the radical R, the formula ROH (III) may represent water, an alcohol and an acid, or a salt thereof, that is to say, compounds of which the physical properties, for example solubility and miscibility, and the general chemical behaviour, frequently lie far apart and thus may considerably influence the course of the reaction according to the invention. Because of this, the especially advantageous and preferred process conditions for each such type of compound are to be chosen in each specific case.

If free hydroxyl (R=H) is to be introduced as a result of the exchange according to the invention, the reaction is carried out in aqueous medium; to improve the solubility conditions organic solvents may be added to the reaction mixture, for example alcohols, especially lower alkanols such as methanol, ethanol or isopropyl alcohol, or other water-miscible highly polar aprotic solvents of the dimethyl sulphoxide, dimethylformamide or hexamethylphosphoric triamide type. The reaction is mainly carried out under weakly basic conditions, especially at a pH of between 7.0 and approximately 10.0, wherein, in certain circumstances, the course of the reaction may be even further influenced by a narrower selection of the pH value. If the operation is carried out in a pH range around 9.0, then 25-O-deacetyl-3-hydroxyrifamycin S (I; R=R'=H) is mainly obtained, at a pH of below approximately 8.0, on the other hand, the ester grouping in the 25-position is not affected and 3-hydroxyrifamycin S is obtained. To get the desired pH, salts of alkali metal are advantageously used, such as, especially, salts of sodium and potassium, with weak or medium-strength inorganic and organic acids, especially those that are used to prepare buffer solutions, such as, for example, hydrocarbonates, carbonates, primary, secondary and tertiary phosphates, acetates, benzoates, citrates and tartrates. These salts serve preferably at the same time also as hydrogen bromide-binding agents, provided that they are used in an amount which is able not only to neutralise the acidity of the hydrogen bromide (for which purpose potentially one mole equivalent would be sufficient) but also to keep the pH within the desired range; preferably, this amount does not go below 2 mole equivalents. If the simultaneous deacetylation in the 25-position is desired, sodium bicarbonate, sodium carbonate or potassium carbonate are preferably used, but if, on the other hand, the 25-O-acetyl group is to be retained, sodium acetate or a suitable phosphate buffer is largely used.

If a 3-ether group OR (R=hydrocarbyl) is to be formed by the exchange according to the invention, then the operation is mainly carried out in an excess of the reactant, that is to say, in the corresponding alcohol ROH, which at the same time acts as solvent, and in the absence of water. One of the above-mentioned carboxylic acids and especially an alkali metal salt of a carboxylic acid can be used as the hydrogen bromide-binding agent, such as, especially, sodium acetate, which then imparts to the mixture also the necessary weakly basic reaction. Chiefly, however, only a minimal amount, not exceeding approximately 2 mole equivalents of this auxiliary agent is to be used, in order to confine side reactions, mainly the exchange of bromine for the acetoxy group, within limits.

If by the exchange according to the invention an esterified 3-hydroxyl group OCOR$^1$ is to be introduced, then as exchange agent there is used preferably an alkali metal salt of the carboxylic acid $R^1COOH$ to be introduced, especially the sodium salt, which is used mainly in excess, that is, in an amount of at least 2 mole equivalents. (As mentioned above, the reagent at the same time binds the hydrogen bromide that has formed and imparts to the mixture the weakly basic reaction.) However, a free acid may also be used, and its salt can be allowed temporarily to form directly in the reaction mixture by means of an equivalent amount of an alkali metal bicarbonate or carbonate. As solvent preferably an anhydrous aprotic polar solvent is used, such as, especially a lower alkanoic acid amide, for example, N,N-dimethylacetamide, N,N-diethylacetamide and, more especially, N,N-dimethylformamide, or a di-lower alkyl sulphoxide, such as dimethyl sulphoxide, or hexamethylphosphoric triamide.

The starting materials of the formula ROH are known compounds or are available analogously to these by known processes.

In the primary reaction mixture there are usually present side by side both oxidation stages of the end product, that is to say, the 1,4-quinone form of the S series and the 1,4-hydroquinone form of the SV series. Advantageously, however, the entire product is isolated in only a single of the two forms, preferably in the quinone form. For this purpose, the crude reaction mixture is treated with an oxidising agent, especially one that is customary for oxidising known hydroquinones, for example ammonium persulphate, hydrogen peroxide, atmospheric oxygen or, preferably, potassium ferricyanide; the oxidation takes place mainly under basic conditions. If the end product is required to be isolated in the hydroquinone form (as a rifamycin SV derivative), the crude reaction mixture is treated with a customery quinone-reducing agent, such as hydrosulphite, dithionite or especially ascorbic acid or zinc-glacial acetic acid. In the same way, individual end products of both series may also be converted into one another.

The present invention includes also the already known 3-hydroxyrifamycin, provided that it is prepared by the process according to the invention, and especially the new 3-hydroxyrifamycin S derivatives of the general formula IA

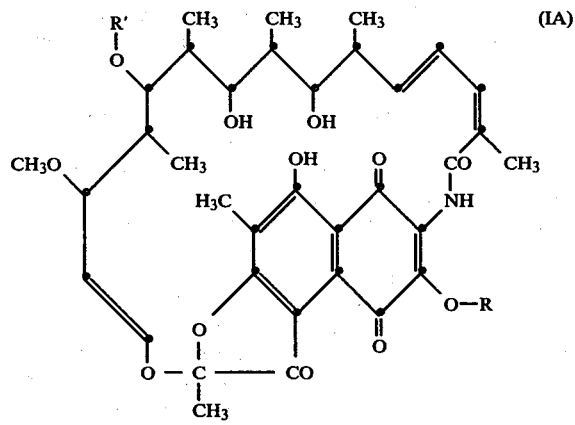

in which each of R and R' represents a hydrogen atom or R' represents acetyl and R represents an optionally substituted hydrocarbyl or the acyl of a carboxylic acid, and the corresponding rifamycin SV derivatives having the 1,4-hydroquinone structure, and also pharmaceutical compositions and preparations in dosage form which contain these 3-hydroxyrifamycin S derivatives, and processes for the manufacture of the same. The subject of the invention is also the use of the new 3-hydroxyrifamycin S derivatives and the corresponding pharmaceutical products as antibiotics, especially antimicrobial agents and especially agents that act against cocci and bacteria, and also the medical methods for treating infections, especially bacterial infections, in warm-blooded animals, especially in humans, and also in domestic animals by the administration of these compounds or their pharmaceutical forms.

The above-characterised 3-hydroxyrifamycin S derivatives according to the invention may be used as valuable chemotherapeutic agents in this field by virtue of their antibiotic, especially antimicrobial, properties. They may also be used as additives for animal feedstuffs and to preserve foodstuffs and as disinfectants. Furthermore, they may serve also as intermediates for the manufacture of other useful compounds, especially antibiotically active rifamycin derivatives.

With regard to the antimicrobial use, particular emphasis should be placed on compounds of the formula I in which R' represents acetyl and R represents a radical Alk of lower aliphatic character, an aromatic radical Ar or an acyl radical of the formula $R^2CO-$ in which $R^2$ represents hydrogen, Alk or Ar.

The aromatic radical denoted by the symbol Ar is an unsubstituted or substituted carbocyclic monocyclic aryl or heterocyclyl, such as, for example, phenyl, 2- and 3-furyl, 2- and 3-thienyl, 2-, 3- and 4-pyridyl, 2- and 5-pyrimidyl, 2-imidazolyl or 5-tetrazolyl. These radicals, especially phenyl, may carry one or more of the following substituents: lower alkyl, such as ethyl and especially methyl, halogen atoms, such as fluorine, chlorine and bromine, nitro, hydroxy, lower alkoxy, such as ethoxy and especially methoxy, methylenedioxy, formyl, carboxyl, lower alkoxycarbonyl, such as methoxy- and ethoxycarbonyl, amino, di-lower alkylamino, such as diethylamino and dimethylamino, and acylamino, such as lower alkanoylamino, especially acetamino.

The radical of lower aliphatic character denoted by the symbol Alk is an optionally substituted lower alkyl or lower alkenyl, or a corresponding cycloalkyl or cycloalkenyl having at most 7 carbon atoms. These radicals may carry one or several optionally substituted aromatic radicals Ar, and/or be substituted by one or more of the following functional groups: hydroxyl, lower alkoxy, such as methoxy and ethoxy, aryloxy, such as phenoxy or optionally substituted, as mentioned above for the radical Ar. phenoxy, lower alkanoyloxy, such as formyloxy and acetoxy, oxo, such as aldehydo and keto, and also the corresponding acetals and ketals, especially those with lower alkanols or lower alkane-(1,2- or 1,3-)diols, carboxyl, carbamoyl, lower alkoxycarbonyl, such as methoxycarbonyl and ethoxycarbonyl, nitro, and disubstituted amino, such as dimethylamino. Among the unsubstituted lower alkyl and lower alkenyl radicals, and among the corresponding cycloaliphatic analogues, in particular those mentioned initially are preferred; among the corresponding substituted radicals the following may be mentioned as examples: a hydroxyalkyl, for example hydroxymethyl, 2-hydroxyethyl, 2- and 3-hydroxypropyl, 4-hydroxybutyl and their esterified, especially acetylated, form, such as 2-formyloxyethyl and 2-acetoxyethyl, 4-oxopentyl, a lower alkoxy-lower alkyl, for example methoxymethyl, 2-methoxyethyl and 2-ethoxyethyl, a carboxy-lower alkyl, such as carboxymethyl, 1- and 2-carboxyethyl, 3-carboxypropyl and 4-carboxybutyl, and also corresponding radicals in which the carboxyl group is present as an amide or an ester, especially a lower alkyl ester, for example ethyl ester and especially methyl ester. Examples of a lower alkyl or lower alkenyl substituted by aromatic radicals Ar are in particular the following: benzyl, diphenylmethyl, furfuryl, thenyl, 2-phenylethyl, styryl and cinnamyl, which may also be substituted in the above-mentioned manner.

In the acyl $R^2CO-$, $R^2$ may have all the above-mentioned meanings of Alk and Ar, and preferably $R^2CO-$ is the radical of an optionally substituted lower alkane-, lower alkene-, aryl- or heterocyclyl-carboxylic acid or is the formyl radical. Among preferred functional groups which occur in such substituted carboxylic acids are: hydroxy, methoxy, halogen, especially chlorine, nitro, lower alkoxycarbonyl, especially methoxycarbonyl, and di-lower alkylamino, especially dimethylamino, and in the case of the aromatic groups, also formyl, methylenedioxy and primary amino. Among especially preferred lower alkane- or lower alkenecarboxylic acid radicals the following deserve special mention: acetyl, propionyl, butyryl, chloroacetyl, trifluoroacetyl, nitroacetyl, glycoloyl, lactoyl, 4-oxopentanoyl, methoxyacetyl, methoxalyl, ethoxalyl, N,N-dimethylglycyl, glutaminyl, acryloyl, methacryloyl, crotonoyl, phenylacetyl, cinnamoyl, phenoxyacetyl, 2-furylacetyl, 2-furanacryloyl, 4-pyridinepropionyl. Among preferred radicals of arylcarboxylic and heterocyclylcarboxylic acids the following deserve special mention: benzoyl, p-nitrobenzoyl, p-methoxybenzoyl, p-chlorobenzoyl, o-, m- and p-toluoyl, 2,4,6-trimethylbenzoyl, salicyloyl, p-hydroxybenzoyl, furoyl, thenoyl, 2-pyridinecarbonyl, nicotinoyl, isonicotinoyl, and 1-and 5-tetrazolecarbonyl.

These new compounds are distinguished by their valuable pharmacological properties: thus, according to results in vitro, they possess antibiotic, especially antibacterial, properties, such as, firstly, against gram-positive and gram-negative cocci, such as *Staphylococcus aureus, Streptococcus pyogenes, Streptococcus pneumoniae, Neisseria meningitis, Neisseria gonorrhoae* (in the tested concentration range of from 0.01 to 8 mcg/ml), and secondly against gram-negative bacilli, such as *Enterobacteriaceae, Pseudomonas aeruginosa, Haemophilus influenzae* (in the tested concentration range of from 0.01 to 64 mcg/ml). Active substances deserving of special emphasis are 3-acetoxy-, 3-benzoyl-, 3-phenoxy-, 3-(2-methoxyethyl)- and especially 3-methoxy-rifamycin S, which all have a marked inhibiting action even at the mentioned lowest concentration.

In accordance with these favourable properties, the invention also includes the use of the new 3-hydroxyrifamycin S derivatives, alone or in combination with another antibiotic or chemotherapeutic agent, as an agent to combat infections that are caused by bacteria of cocci, for example those mentioned, namely both as a drug and a disinfectant. When used as a drug, the active substance according to the invention is preferably administered in the form of a pharmaceutical preparation together with at least one conventional pharmaceutical carrier or adjunct, to a warm-blooded animal, especially humans.

For the purpose of manufacturing pharmaceutical preparations, each individual one of the compounds according to the invention, especially one of those given special emphasis, can be mixed with an inorganic or organic carrier material suitable for topical, enteral or parenteral administration. For this purpose those substances that do not react with the new compound can be considered, such as, for example, gelatin, lactose, starch, magnesium stearate, vegetable oils, benzyl alcohol, or other medicament carriers. The pharmaceutical preparations may be in the form of, for example, tablets, dragees, powders and suppositories, or in liquid form as solutions, suspensions, emulsions, creams or ointments. If desired, they may be sterilised and/or contain adjunts, such as preservatives, stabilisers, wetting agents or emulsifiers. They may also contain other therapeutically valuable substances. The disinfectants also may be mixed with suitable carrier substances, as is known.

The dosage of the active substances, for example the 3-hydroxyrifamycin S derivatives especially emphasized above, is effected in principle in the same manner as those of recognised antibiotics of the rifamycin type; it depends, however, firstly on the species, body weight, age and individual condition of the warm-blooded animal, and, secondly, on the method of administration and especially on the particular sensitivity of the causative organism, which can be determined in known manner in a routine test.

The invention also relates to a method for killing or inhibiting the growth (i.e. inhibition) of a microorganism sensitive to at least one of the 3-hydroxyrifamycin S derivatives according to the invention, which is characterised by treating this microorganism, or a medium infected by this microorganism, with an antimicrobially effective dose of one of the 3-hydroxyrifamycin S derivatives according to the invention. The term "antimicrobially effective dose" means an amount of the active substance that is sufficient for an effective inhibition of the particular microorganism to be treated.

The following examples illustrate the above-described invention; they are not, however, intended to limit its scope in any way. Temperatures are given in degrees Centigrade. The composition of solvent mixtures is specified in volume ratio.

EXAMPLE 1

A solution of 3.0 g of 3-bromorifamycin S in 50 ml of methanol and 70 ml of phosphate buffer of pH 8.0 (0.065 mole of $Na_2HPO_4$ and 0.004 mole of $KH_2PO_4$ per liter of water) is refluxed for 4 hours. The colour of the reaction solution changes during this time from blue-violet to yellow-brown. The reaction solution is then oxidised with excess potassium ferricyanide and, after acidification to pH ~3, is extracted with chloroform. After drying and concentration by evaporation of the chloroform extract, the residue is dissolved in ether and the ether solution is exhaustively extracted with phosphate buffer of pH=6. The wine-red aqueous buffer extract is acidified until the colour changes to yellow, and the precipitated 3-hydroxyrifamycin S is taken up with chloroform. After evaporating off the chloroform, 3-hydroxyrifamycin S is obtained in the form of a yellow foam, and the fact that it is identical with the fermentation product obtained earlier can be verified by thin-layer chromatography, 360-MHz-$^1$H-NMR spectra, and by UV and IR spectra.

EXAMPLE 2

A mixture of 1.0 g of 3-bromorifamycin S, 0.5 g of anhydrous sodium acetate and 30 ml of methanol is heated in a pressure tube for 5 hours at 75°. The reaction mixture is concentrated by evaporation, acidified with citric acid, and chromatographed on silica gel with chloroform/acetone (19:1) as eluant. The material eluted first consists of pure 3-methoxyrifamycin S; 100-MHz-$^1$H—NMR spectrum (in CDCl$_3$): no signal for H-3; 4.16 ppm (s, 3H, OCH$_3$ at C-3); UV spectrum (ethanol; nm/$\epsilon_{max}$): 215/26900, 268/23400, ~300 (shoulder), ~350 (shoulder), 396/4360; IR spectrum (CH$_2$Cl$_2$): 3500 (OH), 3400 (NHCO), 1735 (ester, 5-ring ketone), 1670 (amide-I, quinone-CO), 1640 (quinone-CO linked) cm$^{-1}$; mass spectrum; m/e=725 (C$_{38}$H$_{47}$NO$_{13}$), intense fragments: 709, 693, 695, 635, 303, 423 etc.

EXAMPLE 3

A solution of 1.0 g of 3-bromorifamycin S in 30 ml of 2-methoxyethanol which contains in suspension 0.5 g of anhydrous sodium acetate, is heated, whilst stirring, for one hour at 90° and concentrated by evaporation. The residue is treated with citric acid and chromatographed on silica gel with methylene chloride/acetone (19:1) as eluant. The resulting 3-(2-methoxyethoxy)rifamycin S is characterised in the following way: 100-MHz-$^1$H—NMR spectrum (in CDCl$_3$): signals of the C-3 substituent at 3.36 (s, 3H, OCH$_3$), ~3.7 (m) and 4.62 (m, OCH$_2$CH$_2$OCH$_3$) ppm.

EXAMPLE 4

0.75 g of anhydrous sodium acetate is added to a solution of 1.5 g of 3-bromorifamycin S and 0.75 g of phenol in 30 ml of dimethyl sulphoxide and the whole is heated for 3 hours at 90°. After cooling, aqueous potassium ferricyanide solution is added in excess to the reaction mixture and the whole is acidified with citric acid; the reaction products formed are taken up in chloroform. By chromatography on silica gel with chloroform/acetone (19:1) the material contained in the chloroform extract yields firstly 3-bromorifamycin S, then the desired 3-phenoxyrifamycin S; 100-MHz-$^1$H—NMR spectrum (in CDCl$_3$): signals of the phenoxy substituent at 6.8–7.4 (m, 5H) ppm; UV spectrum (0.01 N alcoholic hydrochloric acid, nm/$\epsilon_{max}$): 220/34600, 266 (shoulder), 270/24800, 342/6000, 400 (shoulder).

EXAMPLE 5

A mixture of 2.0 g of 3-bromorifamycin S with 2 g of anhydrous sodium acetate and 50 ml of dimethylsulphoxide is heated for one hour at 90°. During this time the initially blue-violet colour of the reaction mixture turns to brown-red. Aqueous potassium ferricyanide solution is then added in excess, the mixture is acidified with citric acid and the reaction products formed are taken up with ether. From the ether solution 3-acetoxyrifamycin S is extracted by repeated shaking with phosphate buffer of pH 6.0. The combined aqueous buffer extracts are acidified with citric acid, and the precipitated 3-acetoxyrifamycin S is taken up with chloroform. After drying and concentration by evaporation of the chloroform extract, almost pure 3-acetoxyrifamycin S is obtained which crystallises from ether in the form of light yellow needles, m.p. 154°–155°. Mass spectrum: m/e=753 (C$_{39}$H$_{47}$NO$_{14}$), characteristic fragments at: 723, 721, 713, 711, 705, 695, 693, 663, 661. 100-MHz-$^1$H—NMR spectrum (in CDCl$_3$): signals of 2-acetyl groups at 2.10 (s, 6H), ppm; UV spectrum (0.01 N alcoholic hydrochloric acid, nm/$\epsilon_{max}$): 226/33100, 273/26700, 340/6200, 390/4260.

EXAMPLE 6

A mixture of 2.0 g of 3-bromorifamycin S with 2 g of anhydrous sodium benzoate and 30 ml of dimethylformamide is heated for two and half hours at 70°. During this time, the initially blue-violet coloured reaction mixture changes its colour to brown-red. Aqueous potassium ferricyanide solution is then added in excess, the mixture is acidified with citric acid and the reaction products formed are taken up with ether. The 3-benzoyloxyrifamycin S is extracted from the ether solution by repeated shaking with phosphate buffer of pH=6.0. The combined aqueous buffer extracts are acidified with citric acid, and the separated 3-benzoyloxyrifamycin S is taken up with chloroform. After drying and concentration by evaporation of the chloroform extract, 3-benzoyloxyrifamycin S is obtained; mass spectrum: after silylation m/c 1031 (tris-trimethylsilyl derivative of 3-benzoyloxyrifamycin S). 100-MHz-$^1$H-NMR spectrum (in CDCl$_3$): signals of the benzoyl group at 7.3–8.1 (m, 5H) ppm.

EXAMPLE 7

A mixture of 2.0 g of 3-bromorifamycin S, 1.0 g of sodium acetate, 1.0 g of p-hydroxybenzaldehyde and 30 ml of acetonitrile is heated in a pressure tube for 2 hours at 100°, and concentrated by evaporation. The residue is taken up in ethyl acetate, washed with aqueous citric acid solution, dried and concentrated by evaporation. Chromatography on silica gel with methylene chloride/acetone (98:2) as eluant yields firstly traces of rapidly migrating material, and then, as the main fraction, 3-(4-formylphenoxy)rifamycin S, which, after concentration by evaporation, is obtained as a yellow foam. 100-MHz-$^1$H—NMR spectrum (CDCl$_3$): signals of the aromatic H in AB spectrum centred at 7.07 and 7.8 (J*~9Hz, 4H); aldehyde signals at 12.7 (S, 1H) ppm. IR spectrum (CH$_2$Cl$_2$): 3475 (OH), 3380 (NH), 2730 (OH), 1740 (5-ring-CO), 1705 (ester, CHO), 1675 (amide I), 1645 (quinone) 1620 (quinone), 1600 (C=C ring vibration) cm$^{-1}$ etc.; UV spectrum (0.01 N alcoholic hydrochloric acid, nm/$\epsilon_{max}$) 214/38000, 269/34000, 345/6400, 400 (shoulder).

EXAMPLE 8

In the same manner of operation as described in Example 1, but using sodium carbonate instead of the phosphate buffer, in the described manner 25-O-deacetyl-3-hydroxyrifamycin S is obtained as a yellow powder. The 100-MHz-$^1$-H—NMR spectrum (CDCl$_3$ is analogous to that of 3-hydroxyrifamycin S, but lacks the signal of the CH$_3$CO.O-group placed at 2.1 ppm. What is claimed is:

1. Process for the production of a rifamycine derivative of the S series of the formula

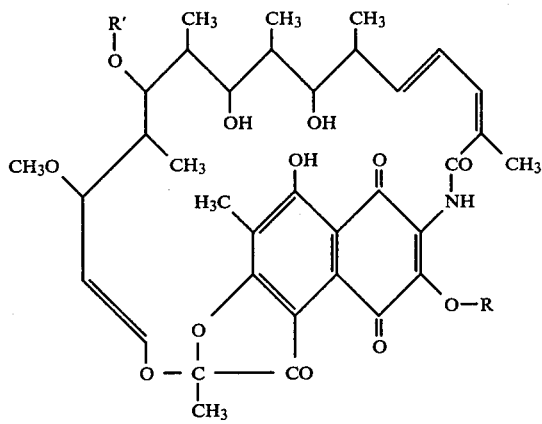

(I)

in which each of R and R' represents a hydrogen atom, or R' represents acetyl and R represents hydrogen, a radical Alk or a radical Ar or the acyl radical $R^2$—(C=O)— which $R^2$ is hydrogen, Alk or Ar, whereby Alk represents an alkyl radical having a maximum of 7 carbon atoms or such an alkyl substituted with hydroxy or alkoxy having a maximum of 4 carbon atoms, and Ar represents phenyl or a phenyl substituted with lower alkyl, lower alkoxy, methylendioxy or formyl, or of an analogous derivative of the SV series, wherein 3-bromorifamycin S of the formula

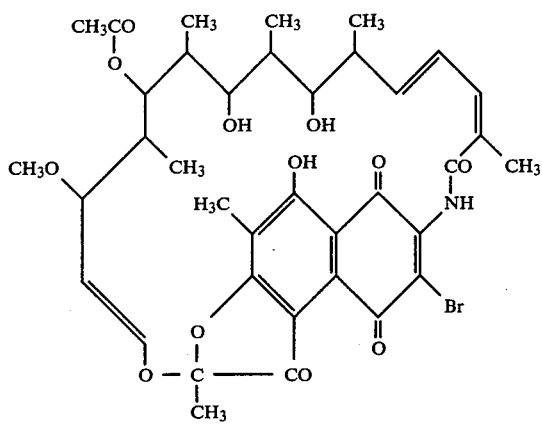

(II)

is treated with a compound of the formula ROH (III) in which R has the meanings mentioned above, or with a salt thereof, in a neutral to basic medium not exceeding pH 10.0 and, optionally, in the presence of a hydrogen bromide-binding agent and/or an organic solvent, at atmospheric or slightly elevated pressure and temperatures between +20° to +140°, and the product is isolated in the form of a derivative of the S series of SV series.

2. Process according to claim 1, characterised in that, to prepare a compound of the formula I in which R represents hydrogen, the starting material of the formula II is heated in an aqueous medium in the presence of a water-miscible polar aprotic organic solvent at a pH of between 7.0 and 10. 0.

3. Process according to claim 2, characterised in that, by performing the reaction in a pH range around 9.0, 25-O-deacetyl-3-hydroxyrifamycin S of the formula I, in which each of R and R' represents hydrogen, is prepared.

4. Process according to claim 2, characterised in that, by performing the reaction in a pH range of between 7.0 and 8.0, 3-hydroxyrifamycin S of the formula I, in which R represents hydrogen and R' represents acetyl, is prepared.

5. Process according to claim 1, characterised in that a compound of the formula I in which R represents Alk or Ar as defined in claim 2 is produced by reacting, the starting material of the formula II with a molar excess of an alcohol ROH wherein R is as specified hereinabove in the presence of at most 2 mole equivalents of an alkali metal salt of a carboxylic acid.

6. Process according to claim 1, characterised in that a compound of the formula I in which R' represents an acyl radical, $R^2Co$— in which $R^2$ represents hydrogen, Alk or Ar as defined in claim 2 is produced by reacting the starting material of the formula II with an alkali metal salt of a carboxylic acid $R^2COOH$ in which $R^2$ is as specified hereinabove, in an anhydrous aprotic polar solvent.

7. A rifamycin S derivative of the formula

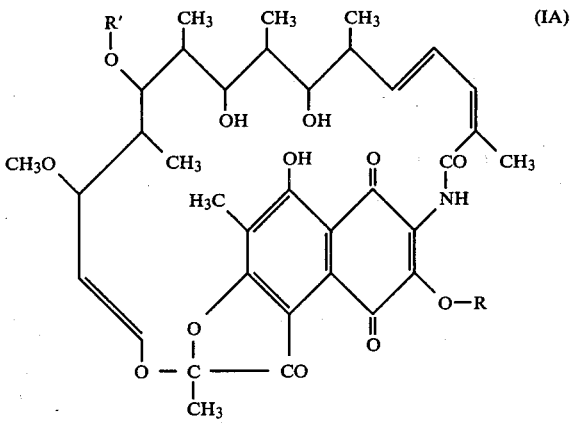

(IA)

in which
each of R and R' represents a hydrogen atom or
R' represents acetyl and R represents a radical Alk or a radical Ar or the acyl radical of a carboxylic acid $R^2$—(C=O)— in which $R^2$ is hydrogen, Alk or Ar, whereby Alk represents an alkyl radical having a maximum of 7 carbon atoms or such an alkyl substituted with hydroxy or alkoxy having a maximum of 4 carbon atoms, and Ar represents phenyl or a phenyl substituted with lower alkyl, lower alkoxy, methylendioxy or formyl,
and a corresponding derivative of the SV series.

8. A compound according to claim 7, in which R' represents acetyl and R represents a lower alkyl lower hydroxyalkyl or lower alkoxy-lower alkyl, and a corresponding derivative of the SV series.

9. A compound according to claim 7 which is selected from the group comprising 3-phenoxyrifamycin S, 3-acetoxyrifamycin S, 3-benzoylrifamycin S, 3-(4-formylphenoxy)rifamycin S and 25-O-decetyl-3-hydroxyrifamycin S.

10. A compound according to claim 7 which is 3-Methoxyrifamycin S.

11. A compound according to claim 7 which is 3-(2-Methoxyethoxy)rifamycin S.

12. A pharmaceutical preparation for combating microbial infections containing an antimicrobially effective amount of compound according to claim 7 together with a pharmaceutical carrier.

13. Therapeutic method for inhibiting or relieving microbial infections in a warm-blooded animal, characterised by the administration to these warm-blooded animals of a compound according to claim 7, alone or in the form of a preparation, in amounts which in these warm-blooded animals are effective to inhibit or relieve the infection.

* * * * *